United States Patent [19]

Oh

[11] Patent Number: 4,946,774

[45] Date of Patent: Aug. 7, 1990

[54] PROCESS FOR DETECTING CANCER AND FOR MONITORING THE EFFECTIVENESS OF CANCER THERAPY

[75] Inventor: Se-Kyung Oh, Brookline, Mass.

[73] Assignee: Trustees of Boston University, Boston, Mass.

[21] Appl. No.: 118,719

[22] Filed: Nov. 9, 1987

[51] Int. Cl.$^5$ .................. G01N 33/53; G01N 33/536; C07K 15/00; C12N 15/00

[52] U.S. Cl. ........................................ 435/7; 436/501; 436/536; 436/548; 436/64; 436/813; 530/350; 530/380; 935/110

[58] Field of Search ................... 435/7, 240.27, 172.2, 435/68, 64; 436/548, 536, 813, 601; 530/387, 413, 415, 350, 380; 935/110; 424/101

[56] References Cited

U.S. PATENT DOCUMENTS

| | | | |
|---|---|---|---|
| 4,537,712 | 8/1985 | Oh | 530/413 |
| 4,720,385 | 1/1988 | Lembach | 530/364 |

OTHER PUBLICATIONS

Oh et al., Cancer Res., Oct. 1, 1987, vol. 47(19), pp. 5120–5126.

Weiss et al., Cancer Detect. Prev., 1981, vol. 4(1–4), pp. 211–217.

Israel et al., Biomedicine, Oct. 1978, vol. 28(5), pp. 292–297.

Katnik et al., Journal of Immunological Methods, vol. 102, 1987, pp. 279–282.

Wolf et al., Am. J. Surg (U.S.A.), vol. 138/4, 1979, pp. 489–500.

Israel et al., Inserm, vol. 97, 1980, pp. 53–63.

Wiedermann et al., Neoplasma, vol. 26, 1979, pp. 315–324.

Akima et al., Gan to Kagaku Ryoho (Cancer and Chemotherapy), vol. 12(6), 1985, pp. 1278–1285.

*Primary Examiner*—Esther M. Kepplinger
*Assistant Examiner*—Florina B. Hoffer
*Attorney, Agent, or Firm*—Paul J. Cook; Lawrence Gilbert

[57] ABSTRACT

A process for detecting cancer in a human patient is provided wherein a blood serum is recovered from the patient and is reacted with a monoclonal antibody comprising anti-haptoglobin variant under conditions to effect an immunoreaction when an immunosuppressive factor having a molecular weight of about 50K Daltons is present in the serum. The presence of immunosuppressive factor at concentration levels substantially exceeding normal concentration levels indicates the existence of immunoincompetence due to widely spread cancer. The effectiveness of cancer therapy is monitored by monitoring the change in levels of the immunosuppressive haptoglobin variant factor in the serum from the patient being treated.

2 Claims, 4 Drawing Sheets

PROCESS FOR DETECTING CANCER AND FOR MONITORING THE EFFECTIVENESS OF CANCER THERAPY

BACKGROUND OF THE INVENTION

The Government has rights in this invention under Grant Nos. CA 15129 and ST 32-CA 09423 from the National Institute of Health.

This invention relates to a process for assaying for wide spread cancer and for monitoring the effectiveness of cancer therapy for a patient.

Prior to the present invention, a process had been disclosed in U.S. Pat. No. 4,537,712 for purifying an immunosuppressive compound derived from malignant ascites fluid or from Cohn fraction IV. The patent discloses that a composition having the immunosuppressive activity can have a minimum molecular weight of about 50,000 which further reduces to 38K and 18K Da components.

It has been disclosed that macromolecular complexes having immunosuppressive activity were known to suppress T-dependent antibody responses in vivo and T-Dependent mitogen responses in vitro at microgram concentrations per ml, Oh et al, Fed. Proc. 39:1164, 1980. However, the nature and mechanism of immune suppression are not fully understood. Specific unresponsiveness to tumor associated antigens has been reported in a number of experimental systems. In addition, non-specific suppression of a broad spectrum of immune responses may occur. Correlated with the latter phenomenon is the presence of non-specific immunosuppressive factors in sera and ascites fluids of cancer patients. These factors are not only associated with cancer however. Non-specific immunosuppressive factors have also been detected in blood and urine in a variety of conditions, including experimental amyloidosis, pregnancy, liver disease and normal human serum. It has been unclear, therefore, whether immunosuppressive factors associated with cancer are unique products of tumor cells or whether they resemble substances found in other conditions and perhaps represent a normal feed-back mechanism that has been deranged during the development of tumor.

An impaired immune response has been thought to be associated with the etiology and/or pathophysiology of neoplasia. Although the mechanisms involving this immune suppression are highly complex and remain largely unknown, a variety of substances have been suggested to nonspecifically contribute to the defective immunity. Subsequently, a depressed immune status in cancer patients has been correlated with high levels of such immunoregulatory factors. These factors are generally found in the plasma and may consist of acute phase reactant proteins of hepatic origin, factors produced by tumors, or host factors produced in response to tumor growth. Thus, observed alterations in these immunosuppressive factors as possible indications of patients' immune status, as well as a functional aid in the clinical monitoring of disease and response to anti-cancer therapy are of interest.

The Acute Phase Response (APR) results in a characteristic pattern of alterations in the concentration of a number of plasma proteins termed Acute Phase Proteins (APP). Haptoglobin (Hpt), alpha-1-acid glycoprotein (AGP), alpha-1-antitrypsin (AT), and C-reactive protein (CRP) represent a few of the "positive" APP which increase during the APR while albumin represents a "negative" APP which decreases during the APR. Although the specific behavior of the individual APP may vary, they all modulate the host immune response to restore the homeostatic balance disturbed by tissue injury or infection. Consequently, an unregulated APR may function to depress the cellular immune response, and a lack of the APR may induce autoimmune reactivity to the damaged tissue.

There has been considerable interest in the APR of patients with cancer. Early studies confirmed that advanced cancer is frequently accompanied by a rise of alpha globulins which has been attributed, at least in part, to APP. In fact, serum protein levels have been studied in cancer patients and demonstrated that serum levels of certain APP including Hpt, AGP, AT and CRP, were elevated while others such as albumin were diminished. The degree of elevation was not particularly characteristic of any specific type of tumor but was more definitive in malignancy and reflected tumor load and severity of disease as observed in ovarian cancer, renal cell carcinoma, lung cancer, bladder cancer and breast cancer. Thus, the evidence suggests that APP are not specific markers for cancer, but may play a significant role in monitoring the development of tumor, especially as it relates to tissue damage, and as a possible indicator of therapeutic efficacy.

It has been demonstrated that sera from cancer patients inhibits the lymphocyte response to plant mitogens. In fact, it has been shown that the APP and other normal serum pro- proteins can depress lymphocyte responsiveness. It has been shown that a correlation exists between elevated serum glycoprotein levels and depressed cellular immunity, both in vivo and in vitro, and that circulating levels of AGP and Hpt may be more related to immune status than tumor extent and may be involved in the inhibition of the host immune response to tumor.

In addition to these immunosuppressive APP, it has been suggested that active immunosuppressive substances might be produced or induced by tumor cells and secreted into body fluids. In fact, lymphocyte inhibitory activity has been found in the ascitic fluids of cancer patients and several murine tumor models. This further indicates that malignant neoplasia is often associated with excess production of immunosuppressive factors. The immunosuppressive substance named Suppressive E Receptor factor (SER) from the ascites fluid of patients with malignant ovarian cancer inhibits the E-rosetting phenomenon of human T lymphocytes is disclosed in U.S. Pat. No. 4,537,712. It would also be desirable to have a utility for the immunosuppressive factor as a means for detecting a disease state and/or for monitoring the effectiveness of therapy for treating a disease state.

SUMMARY OF THE INVENITON

The present invention is based upon the discovery that the high molecular weight species of the immunosuppressive factor constitutes a variant of haptoglobin comprising a subunit of a molecular weight of 38–40K Daltons covalently bonded to another subunit of a molecular weight of 17–19K Daltons. The low molecular weight residue comprises the alpha-2 subunit of haptoglobin while the high molecular weight residue comprises the beta subunit of haptoglobin. Based upon this discovery, antibody to this haptoglobin variant can be utilized to determine the presence of the immunosuppressive factor in human serum. If the presence of a high concentration of a variant of haptoglobin immunosuppressive factor is determined to be present, the patient from which the serum is obtained is determined to have a wide spread malignancy. In addition, the effectiveness of therapy to such a patient can be monitored by monitoring the change in immunosuppressive factor, a variant of haptoglobin in the patient's sera.

DETAILED DESCRIPTION OF SPECIFIC EMBODIMENTS

Figure 1:
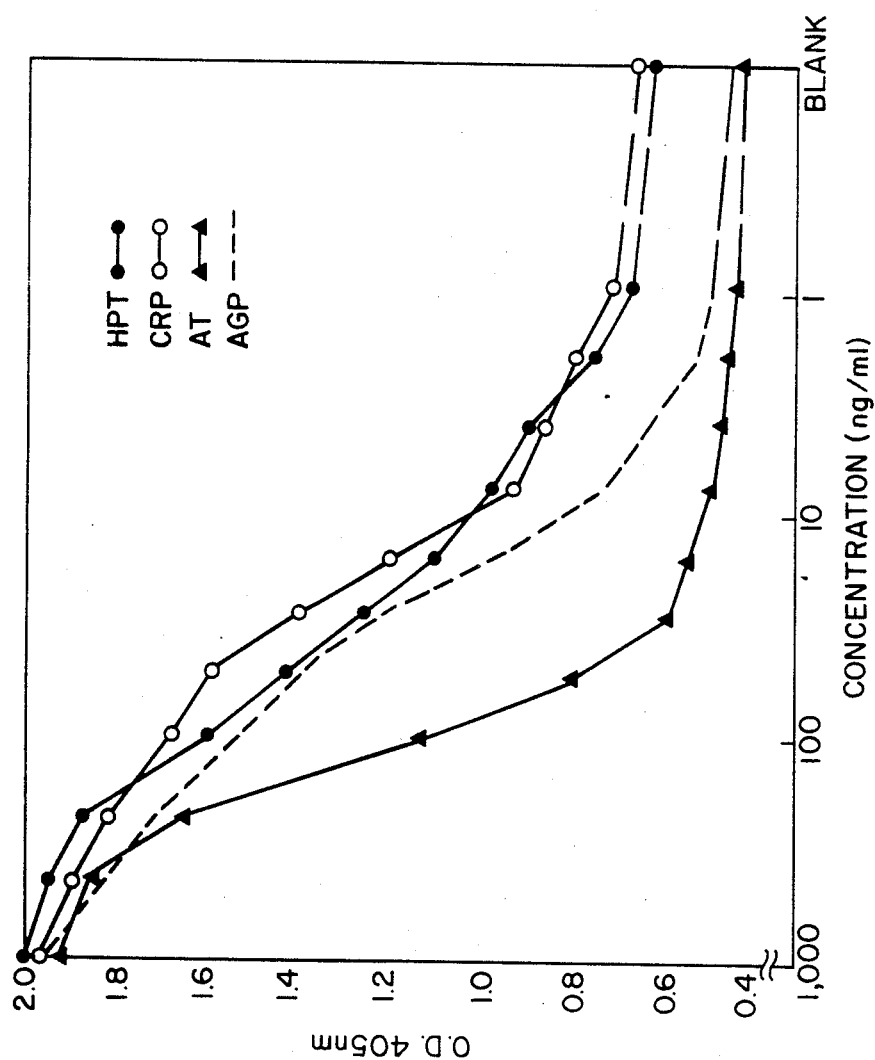

With the exception of the fact that the immunosuppressive factor of this invention comprises a form of haptoglobin, the characteristics of the immunosuppressive factor and one method of isolation are disclosed in U.S. Pat. No. 4,537,712 to Oh which is incorporated herein by reference.

Suprisingly, it has been found that the immunosuppressive factor comprises an abnormal form of haptoglobin comprising a polypeptide having a subunit molecular weight of 38-40K Daltons covalently bonded to another subunit having a molecular weight of 17-19K Daltons. Both the high and low molecular residues are immunoreactive with antibody to haptoglobin. The concentration of the immunosuppressant haptoglobin present in the acites fluid is approximately 10-100 times greater than is present in normal patients. Therefore, by monitoring the concentration of the immunosuppressive haptoglobin in the sera of a patient, the existence in the patient of a malignancy can be determined. Furthermore, by monitoring the change in concentration of the immunosuppressive factor, the effectiveness of the therapy can be determined. A therapy is ineffective when the concentration of the immunosuppressive factor remains the same or substantially increases. A significant decrease in immunosuppressive factor shows the therapy to be effective.

The immunosuppressive factor can be recovered from a body fluid as set forth above or by use of recombinant DNA technology. The gene for producing the immunosuppressive factor can be cloned from ovarian tumor cells into phage lambda GT vector. A probe for the gene which produces the immunosuppressive factor can be radiolabeled and is hybridized with the CDNA library produced from the tumor cells. Selected clones can be isolated and propagated in larger quantities.

EXAMPLE I

The immunosuppressive factor was purified from malignant ascites fluid by partial delipidation, salt precipitation and gel filtration. Further purification of the suppressor factor to an apparent electrophoretic homogeneity was achieved by sequential affinity chromatography on chicken cyanomethemoglobin-conjugated Sepharose concanavalin A-Sepharose and by high performance liquid chromatography on gel filtration column. This immunosuppressive factor obtained from ascites fluid of an ovarian cancer patient was an acidic glycoprotein (isoelectric point 3.6-4.0) of approximately M.W. 50K Da on SDS PAGE under non-reducing conditions. This factor inhibited T-dependent mitogen responses in vitro, T-dependent antibody response in vivo and blocked E-rosetting. This immunosuppressive factor, when found to show serological cross-reactivity with a monoclonal anti-E receptor antibody and to be inhibited by the antibody, was named as suppressive E-receptor (SER) factor. SER, though biochemically similar, may not be identical to the soluble form of E-receptor itself. Therefore, its biochemical identity was determined as set forth herein.

The electrophoretically homogeneous SER moiety can be dissociated into 38-42K Da moieties upon SDS-PAGE under vigorous reducing conditions. Presence of these two components (38-42K and 17-19K Da) was consistent with SER preparations obtained from different primary tumors (pleural effusions of two separate lung cancer patients and ascites fluids from seven different ovarian cancer patients).

Following electro-elution from the SDS-PAGE gel, amino acid composition was determined after hydrolysis with 5.7N HCl at 110° C. for 20 hours and derivatizing them to phenylthiocarbamyl amino acids using the Pcio-Tag station (Waters Asso.). Amino acid sequences of these two peptide compoonents were determined by automated Edman degradation followed by identification of the phenylhydantoid-derivativederivative using the gas phase sequenator (Applied Biosystems). The first 15 amino acid residues from the 17-19K Da and 38-40K Da components were identified to be:

val-asp-ser-gly-asn-asp-val-thr-asp-ileu-ala-asp-asp-gly-x and ileu-leu-gy-gly-his-leu-asp-ala-lys-gly-ser-phe-pro-trp-gin-gin respectively, thus identifying them as the alpha-2 and beta subunits of haptoglobin. Table 1 shows that the amino acid compositions of these two components correlate well with the beta and alpha-2 subunits of haptoglobin (linear correlation coefficient of 0.934 and 0.942 respectively.

In order to confirm the identity of SER with haptoglobin, commercial haptoglobin (Sigma Chemical) and graded concentrations of SER were subjected to Western blotting analysis using a goat anti-haptoglobin antiserum (Sigma Chemical). The SER pattern coincides with that of haptoglobin. Presence of contaminating alpha-1-acid glycoprotein (AGP) was demonstrated by Western blotting of the fuplicate gel ran simultaneously. However, AGP content accounted for 3-10% pf the total protein, whereas haptoglobin content was 90% in six different SER preparations analyzed by an enzyme linked immunoassay.

Previous studies indicated that the polyclonal antiserum to human interleukin-1 (IL-1) cross-reacted with SER preparations. Therefore, SER was subjected to Western blotting analysis using the polyclonal antiserum to the recombinant IL-1 beta (Biogen). The alpha-1 and alpha-2 subunits of haptoglobin as well as the SER cross-reacted with polyclonal antiserum to recombinant IL-1 beta (Biogen). However, the level of cross-reactivity was much less than that of the recombinant IL-1 (1-2% of IL-1 beta as examined by an ELISA on haptoglobin using the anti-IL-1 serum). Furthermore, the alpha-2 subunit of haptoglobin showed somewhat higher M.W. (18.5K Da) than that of IL-1 beta (17.5K Da). Serological cross-reactivity of alpha-2 subunit of SER with that of IL-1 is further demonstrated by the ability of the anti-IL-1 immunoadsorbent to absorb out the immunosuppressive activity of SER as shown in Table 2. SDS-PAGE analysis of the supernatant following the immunoadsorption with anti-IL-1 serum removed both of these two components. In contrast, antiserum to human lymphotoxin, or the tumor necrosis factor-alpha, failed to remove the immunosuppressive activity of the SER. SER is much more effective immunosuppressant than that of normal haptoglobin or AGP (at least 100 fold).

However, it was not clear how the haptoglobin moiety in SER retained more potent immunosuppressive property than that of normal haptoglobin or AGP. Previous work of Raam et al, Carcino-Embryonic Protein, Vo; II, F.G. Lehmann ED., Elsevier North Holland Biomedical Press, 599-602 (1979) showed that haptoglobin found in cancer patients (50%) shared immunological cross-reactivity with that of macromolecular haptoglobin isolated from neonatal cord serum. Indeed, the neonatal haptoglobin isolated from neonatal cord serum (in a similar manner as that of SER) exhibited a similar immunosuppressive potency as SER.

Radial immunodiffusion shows that the antiserum to normal adult haptoglobin reacted both with the normal adult haptoglobin as well as with the crude ascites fluids of four different ovarian cancer patients. In contrast, the anti-cord blood serum reacted with purified SER and with the crude ascites fluids obtained from the ovarian cancer patients, but it failed to react with the normal adult haptoglobin. Thus, it suggests that the SER and the haptoglobin contained in the cancer fluids represent a new antigenic determinant that is different from the normal adult type. Purified SER reacted both with anti-normal haptoglobin as well as with anti-cord blood serum. Also shown is the slower mobility of SER-haptoglobin than the normal adult haptoglobin. The beta subunit of SER has somewhat higher M.W. than that of normal adult haptoglobin. As the SER-haptoglobin was isolated from adult patients with tumor, presence of an immunological determinant analogous to neonatal antigen indicates that SER may be a fetal antigen reexpressed during the tumor development. Taken together these data presented above indicate that his neonatal form of haptoglobin also may be responsible for the potent immuno suppressive property of SER.

Acidification of whole serum is said to denature 80% of the haptoglobin in 30 min. and the conventional purification procedure utilizing ion exchange chromatography under acidic conditions might have denatured the native biological activity of haptoglobin. In contrast, the purification procedure herein utilizing purification through affinity columns may have preserved the biological reactivity of haptoglobin better than the conventional purification method.

Serum haptoglobin is an acute phase reactant produced by the liver in response to a cytokine (presumably IL-1 or heptocyte stimulating hormone). Elevated levels of haptoglobin has been reported in the serum of women with inflammatory, benign and neoplastic lesions of the ovary. Elevated levels of haptoglobin has been reported to correlate with the extent of smoking in heavy smoke&s as well as with the tumor load in patients with metastasized tumor. Elevated levels of haptoglobin in serum of tuburculosis patients appears to inversely correlate with their lymphocyte function. Haptoglobin has been isolated from acute phase rabbit serum and showed that the purified haptoglobin significantly inhibits polyclonal mitogenic response of murine splenic lymphocytes to phytohemagglutinin, concanavalin A and lipopolysaccharide.

TABLE 1

| AMINO ACID COMPOSITION OF SER | | |
|---|---|---|
| AMINO ACID | ACTUAL | THEORETICAL No residue/molecule |
| 38-42K Da SUBUNIT VERSUS BETA-2 | | |
| CHAIN OF HAPTOGLOBIN | | |
| ASP | 25.6 | 24 |
| THR | 13.4 | 17 |
| SER | 10.7 | 14 |
| GLU | 28.6 | 25 |
| GLY | 0.0 | 17 |
| ALA | 18.4 | 18 |
| CYS | 0.0 | 4 |
| VAL | 21.7 | 23 |
| MET | 0.0 | 4 |
| ILE | 11.7 | 12 |
| LEU | 20.9 | 20 |
| PRO | 10.8 | 10 |
| TYR | 10.0 | 11 |
| PHE | 7.6 | 7 |
| HIS | 7.8 | 9 |
| LYS | 19.2 | 19 |
| TRP | 0.0 | 5 |
| ARG | 5.3 | 4 |
| 18K Da SUBUNIT VERSUS ALPHA-2 SUBUNIT OF HAPTOGLOBIN | | |
| ASP | 21.8 | 22 |
| THR | 4.6 | 5 |
| SER | 4.0 | 3 |
| GLU | 18.9 | 16 |
| GLY | 0.0 | 12 |
| ALA | 9.0 | 8 |
| CYS | 0.0 | 7 |
| VAL | 11.0 | 12 |
| MET | 0.0 | 0 |
| ILE | 5.5 | 5 |
| LEU | 7.8 | 6 |
| PRO | 10.2 | 11 |
| TYR | 7.6 | 10 |
| PHE | 0.0 | 0 |
| HIS | 3.7 | 4 |

TABLE 2

ABSORPTION OF SER WITH ANTI-IL-1 AND ANTI-HAPTOGLOBIN IMMUNOADSORBENTS
$^3$H-thymidine incorp. to DNA in PHA*-induced mitogenesis (CPM)

| Unstim. | 770 ± 106 |
|---|---|
| Stim. | 30,623 ± 1,770 |
| Purified SER (i ug/ml) | 3,594 ± 1,287 |
| Anti-IL-1-protein A-Seph. absorbed SER | 29,080 ± 3,383 |
| Protein A-Sepharose absorbed SER | 5,054 ± 1,184 |
| Anti-lymphotoxin absorbed SER | 3,971 ± 783 |
| Anti-haptoglobin absorbed SER | 27,636 ± 3,670 |
| Normal Rabbit IgG-Sepharose wash | 30,563 ± 1,353 |

*PHA-phytohemagglutinin. Assays were run in quadruplicate

TABLE 1. Amino acid composition of 40K and 18K Da components of SER shown in comparison to the alpha-2 and beta subunits of haptoglobin. Ten to fifty ug of proteins obtained by electroelution of SDS-PAGE gel (15) was hydrolyzed with gaseous 5.7 N HCl at 110° C. for 20 hours and derivatized as phenylthiocarbamyl amino acids using PicoTag station (Waters Asso.). Resulting phenylthiocarbamul amino acids were analyzed by HPLC as described by Heinrikson and Meredith.

Table 2. Immunoabsorption of SER with anti-IL-1-Protein A-Sepharose and anti haptoglobin-Sepharose.

Polyclonal rabbit antiserum to human haptoglobin (Sigma Chemical) was conjugated to Sepharose 4B (at 10 mg/ml Sepharose beads) by the cyanogen bromide activation method of Cuatrecasas. Normal rabbit serum IgG was conjugateed to Sepharose 4B(10 mg/ml) and used as the control for nonspecific absorption of SER to immunoadsorbent. Two hundred ug of polyclonal rabbit anti-IL-1 (Genzyme, Boston, Mass.) was bound to the protein A-Sepharose (Sigma Chemical, St. Louis, Mo.) at 4° C. for 2 hours and used to absorb the purified SER at 4° C. overnight. The residual activity of SER remaining in the supernatant was assayed for its ability to inhibit the PHA induced mitogenic response of human peripheral blood lymphocytes as described by Cooperband et al.

EXAMPLE 2

This example shows the simultaneous measured changes in the levels of certain APP which have been reported in the literature as being elevated with malignant disease, including Hpt, AGP, AT and CRP, as well as albumin, which decreases in malignancy. In addition, levels of the novel immune suppressor, SER are measured. These observations were made in patients undergoing anti-cancer immunotherapy. This example showed a correlation among these four immunosuppressive APP and SER, including albumin as a negative control, in patients receiving a form of adoptive immunotherapy termed autolymphocyte therapy.

Serum Samples

Serum samples from normal healthy donors (9 females and 10 males), 23 to 93 years old, were used as the control population. Thirty one plasma samples were collected from patients with a variety of autoimmune diseases including Guillain-Barre syndrome, peripheral neuropathy, Myasthenia Gravis, dermatitis, myeloproliferative disorder (thrombocytosis), IgM, IgG, or multiple myelomas and head and neck cancer. Specimens were also collected from 24 patients with a documented bacterial, viral or yeast infection.

Sequential serum samples were obtained from 52 patients with renal cell carcinoma, pancreatic carcinoma, or melanoma who are undergoing autolymphocyte therapy using in vitro immunized autologous lymphocytes. All of these patients had a biopsy-proven disease. Of these 52 patients, 21 were chosen to be examined in this study. All of the patients studied had been on the therapy for at least 3 months and sequential serum samples were available for serological study.

The collected sera/plasma samples were stored at 20° C. until assayed. Samples were then thawed and an aliquot was removed and diluted with phosphate buffered saline. (PBS).

Enzyme Linked Immunosorbent Assay for Acute Phase Proteins

The enzyme-linked immunosorben assay (ELISA) developed to measure levels of APP in patients' sera was performed as follows: 96 well polyvinyl chloride assay plates were coated with 100 ul of capture antibody (goat anti-human Hpt, AGP,or AT; or sheep anti-human CRP diluted 1:1000 with PBS.) Plates were incubated overnight at 37° C. and then washed 3× with PBS containing 0.05% Tween 20 and 3X more with PBS to remove unbound protein and excess salts and detergent. Standard proteins diluted to 1 $\mu$g/ml with PBS were added (100$\mu$l/well) to columns 1 and 2 of the plate in quadruplicate and serially diluted (two fold) to generate a standard curve ranging from 1000 ng/ml to 1 ng/ml. The standard proteins used were haptoglobin types 1-1 or 2-2, CRP (Sigma Chem. Co., St. Louis, Mo.), AGP, and AT. Optimal dilutions of patients' samples were added 100 ul/well in quadruplicate. Plates were then incubated at 4° C. for 1 hour and washed.

The primary antibody, specific to standard antigen, was added next. Rabbit antisera to human Hpt, AGP, or AT (Sigma Chem. Co., St. Louis, Mo.) was diluted 1:1000 in PBS containing 0.05% Tween 20 and added to the microtiter plate (100 $\mu$l/well), except rabbit anti-human CRP (Sigma Chem. Co., St. Louis, Mo.) which was diluted 1:500. Plates were then incubated for 1 hour at 4° C. and washed. 100 $\mu$l of the secondary antibody (goat anti-rabbit IgG (H+L) conjugated to biotin (1 mg/ml PBS; Vector Lab., Inc. Burlingame, Calif.) diluted 1:200 with PBS containing 0.05% Tween 20 was added to each well. Following another 1 hour incubation and washing, 100 $\mu$l of avidin D-glucose oxidase (1 mg/ml PBS) diluted 1:400 (1:350 for CRP assay) in PBS was added to each well. Plates were incubated at room temperature for 30 minutes and then washed.

The final step of the ELISA involved the addition of 100 $\mu$l/ well of chromagenic substrate solution. This solution consisted of 12.5 ml ABTS solution (see below), 1.67 ml 18% glucose, and 0.5 ml horseradish peroxidase (1 mg/ml type VI). The ABTS stock solution, prepared beforehand and stored at 4° C., consisted of: 1 g cacodylic acid, 1.38 g sodium monophosphate, and 20 mg 2,2'-Azinobis (3-ethylbenzothiazoline 6-sulfonic acid) (ABTS) brought up in 100 ml of distilled water. The amount of color which developed in each well was measured at 405 nm using an ELISA reader. The concentration of protein in each sample was determined from the standard curve generated.

Production of Murine Monoclonal Antibody Directed to SER 8 to 24 week old Balb/c mice were immunized i.p. at two week intervals for a total of 3 immunizations with 50 ug of purified SER (34) emulsified in Complete Freund's Adjuvant. Two weeks following the final immunization, animal sera was tested for the presence of antibodies to SER by ELISA. Those animals demonstrating high titers were "rested" for 2-3 months and then challenged by i.v. injection 3 days prior to fusion.

The fusion procedure used to generate these monoclonal antibodies to SER,utilized spleens from immune Balb/c mice were removed, made into a single cell suspension and fused with SP2/0 myeloma cells growing in log phase at a splenocytes: SP2/0 cells ratio of 3:1 with 1 ml of 30% polyethylene glycol 1000. Hybridomas were then resuspended (2–3×10$^6$ spleen cells/ml) and then dispensed (100 ul/well) into 96 well culture plates containing irradiated feeder cells. Feeder cells were peritoneal macrophages from Balb/c mice which were harvested, washed with PBS, resuspended (2–3×10$^4$ cells/ml complete HAT (hypoxanthine, aminopterine thymidine) medium and added to 96 well culture plates (100 $\mu$l/well) at a concentration of 2–3×10$^3$ cells/well one day prior to fusion. The plates were subsequently irradiated (5000 rads) with a Cesium 137 source for 10 minutes.

Hybridomas were maintained with irradiated peritoneal macrophage feeder cells in fresh HAT medium. Wells containing hybridomas producing antibody of desired specificity, as determined by ELISA assay of culture supernatant, were expanded in HT (hypoxantine, thymidine) medium and cloned by a limiting dilution technique. Only those supernatants with high reactivity on SER coated plates and background reactivity on normal adult haptoglobin coated plates were considered to be SER specific antibodies. SER specific monoclonal antibodies thus generated (AH7B8) were used for subsequent SER determinations in patients' sera samples using purified SER as a standard source of antigen.

ELISA to Measure SER

Ninety six well polyvinyl chloride assay plates were coated 100 μl/well with a 1:1000 dilution of capture antibody in PBS (goat anti-human haptoglobin). Plates were incubated overnight at 37° C. and then washed 3× with PBS containing 0.05% Tween 20 and 3× more with PBS to remove unbound protein and excess salts and detergent. Purified SER (1 μg/ml PBS) was used as the standard source of antigen. 100 ul of SER standard was added to columns 1 and 2 of the plate in quadruplicate and serially diluted (two fold) to generate a standard curve ranging from 1000 ng/ml to 1 ng/ml. Optimal dilutions of patients' samples were added 100 μl/well in quadruplicate. Plates were incubated for 1 hour at 4° C. and then washed.

One hundred microliters (100 ul) of the primary detector antibody, SER specific monoclonal antibody containing culture supernatant, was added to each well. Following an additional 1 hour incubation at 4° C. and subsequent washing, 100 μl of the secondary antibody was added. This was an affinity purified goat antibody to mouse IgG and IgM (H+L) conjugated to horseradish peroxidase used at a 1:200 dilution in PBS containing 0.05% Tween 20. The plates were incubated for 1 hour at 4° C. and then washed.

The final step of this ELISA involved the addition of 100 μl/well of substrate solution which consisted of: 12.5 ml mono sodium phosphate-citrate solution (0.1M mono sodium phosphate, imM citrate, pH 4.0), 1 μl hydrogen perodice (30% solution) and 100 μl 2,2'-Azinobis (3-ethylbenzothiazoline 6-sulfonic acid) (ABTS, 0.5 g/10 ml distilled water). The optical density of each well was determined at 405 nm using a spectrophotometer. The concentration of SER in each sample was determined from the standard curve generated.

Determination of Albumin

Serum levels of human albumin were analyzed using a commercial assay kit provided by Seragen Diagnostics, Indianapolis, Ind., which measures the binding of bromcresol green with albumin at 630 nm via the development of bluegreen color. Normal control serum provided in the assay kit and our normal human serum panel were utilized.

Determination of Immunosuppressive Adicid Protein, Circulating Immune Complexes and CA 125

Determinations of immunosuppressive acidic protein (IAP) in patients' sera samples were performed via a gel immunodiffusion technique by Dianon Systems. Quantitation of circulating immune complexes (CIC) in patients' sera samples was performed utilizing a commercial CIC ELISA kit (Cytotech, San Diego Calif.). Levels of ovarian tumor antigen CA 125 were detected utilizing the Centocor CA 125 radioimmunoassay kit (Centocor, Inc., Malvern, Pa.). This procedure uses a radiolabeled monoclonal antibody, OC 125, which reacts with the ovarian tumor associated antigenic determinant CA 125. The bound radioactivity was counted in a gamma scintillation counter and the concentration of CA 125 units was determined from the standard curve generated.

Analysis of Data

Statistical analysis was performed by the Student's t test. A p value $<0.05$ was accepted as a statistically significant value.

Determination of Normal Values for APP and SER

Figure 2:
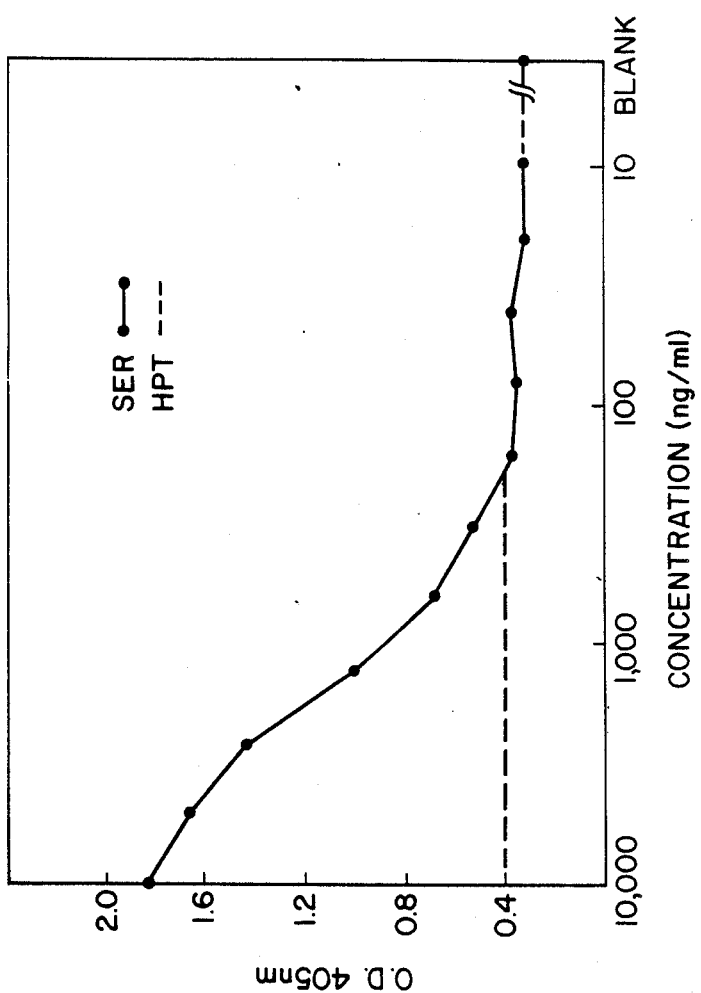

Although normal values for APP's have been reported, it was necessary to reevaluate these values by the ELISA procedure described in materials and methods since the previous values were derived by other methods of quantification. The availability of monoclonal antibody to SER provided a means to quantitatively measure the levels of the immunosuppressive factor, SER, in the serum of normal individuals. FIG. 1 provides typical standard curves generated for each APP. FIG. 2 provides a typical standard curve generated for SER using the monoclonal antibody AH7B8. Serum levels of Hpt, AGP, AT, CRP and SER were measured in our normal population (Table I). The values obtained (mean±standard error) are: Hpt 2.88±18; AGP 0.68±0.07; AT 1.75±0.13; CRP 5.11±2.5; SER 1.06±0.05 The literature values for both the normal and acute phase levels are cited for comparison but the method of determination for these protein levels was not reported. Average values for Hpt and CRP were higher than that reported. Samples for Hpt, AGP and AT were determined at 1:10$^4$ in PBS, 1:10$^2$ for CRP and 1:10 for SER when added to the ELISA plate. The average normal value for albumin was 34.5±0.74 (mg/ml). The reported normal and acute phase values for albumin are 35–40 and 20–30 (mg/ml) respectively.

APP Levels in Nonmalignant Diseases

An initial screening was performed on the serum from patients with a variety of diseases to see if any patterns in the levels of the APP could be detected, especially among a specific type or group of disease(s) (Tables II and III). Those categorized as nonmalignant consisted of individuals with a variety of autoimmune diseases including 2 patients with Guillain-Barre syndrome, 1 patient with peripheral neuropathy, 2 patients with Myasthenia Gravis, and 1 patient with a dermatologic condition and elevated IgE. As expected, those patients with nonmalignant diseases did not demonstrate dramatic changes in levels of any of the APP examined. However, the patient with dermatitis did present elevated levels of Hpt. Since the patient with thrombocytosis, a nonmalignant disorder, showed elevated levels of all three APP, malignant diesase was suspected in this case. It is of interest to note that all patients with either malignant or nonmalignant disease had elevated AGP levels compared to normal controls.

More dramatic elevations were seen within patients with malignancy. The patient with an IgG myeloma presented the largest increase in all three proteins among the four myeloma patients examined. Most interesting were the values obtained through comparison of patients with different stages of both head and neck cancer and renal cell carcinoma. The three patients with either stable disease or a complete response to therapy had very low levels of all three proteins, and in fact had levels of Hpt below the normal value. The most significant changes, however, were noted in patients diagnosed with progressive cancer of either type or in patients having expired. Although the changes were not consistent with any one of the particular APP examined, elevations in all three APP were demonstrated in malignant disease. The profound differences seen among patients in different stages of disease set the foundation for further analysis of sequential changes in these protein profiles among patients undergoing anticancer treatments. It was of even more interest to see how alterations in these proteins relate to CRP levels to indicate possible secondary infection, albumin levels to assess patients' nutritional status and SER levels to enhance the ability to detect disease and monitor patients' response to therapy. A screening of the levels of these APP was thus performed on a group of patients with various bacterial, viral and yeast infections for comparison with levels in patients with malignant diseases (Tabel III).

Changes Observed in APP Levels in Responders

Figure 3:
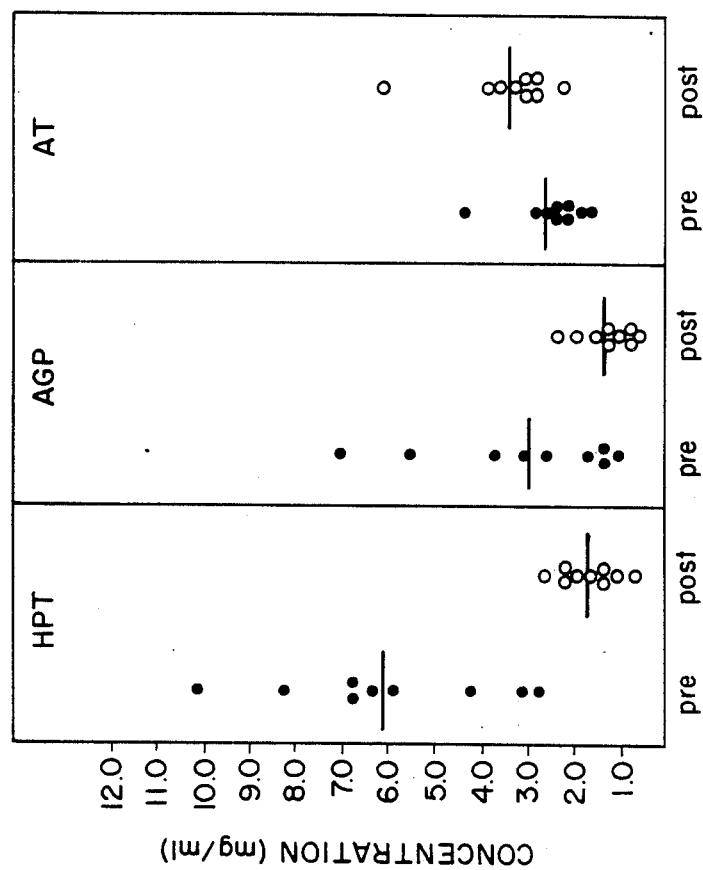

FIG. 3 represents the changes in the levels of Hpt, AGP and AT in those patients responding to autolymphocyte therapy. Responders encompass patients experiencing a complete or partial response or those reaching a stable condition. Nine patients were considered responders including one with melanoma demonstrating a complete response, one a partial response, and the others maintaining a stable condition. For simplicity, a mean value for each protein is listed at at time point at or before the initiation of treatment (pre-treatment) and at least 3 months following the initiation of treatment (post- treatment). Seven out of nine responders had elevated levels of Hpt at initiation of treatment which decreased 3–4 fold three months following treatment. The other two responders had normal pretreatment levels of Hpt and also demonstrated decreases over the course of therapy. All nine responders had levels of Hpt below the normal value at three months or beyond their first treatment. All nine responders had pretreatment AGP levels greater than normal. Seven of these nine demonstrated a 1.5 to 5 fold decrease at least three months beyond initial treatment and AGP levels in three of these seven returned to levels within the normal range. Seven of the nine responders had apretreatment AT levels higher than normal and all responders except one demonstrated increases in the concentration of at least three months past their first treatment. Levels of CRP in these 9 responders ranged from 0.1 to 70.0 ($\mu$g/ml) and levels of albumin ranged from 31.8 to 61.2 (mg/ml) over the course of therapy. These nine responders experienced significant mean decreases in Hpt from $6.08\pm0.8$ to $1.62\pm0.2$, $p<0.001$, in AGP from $3.08\pm0.6$ to $1.37\pm0.2$, $p<0.05$, but a significant mean increase in AT from $2.56\pm0.2$ to $3.38\pm0.3$, $p<0.01$ as analyzed by the Student's t test.

Changes Observed in APP in Progressors

Figure 4:
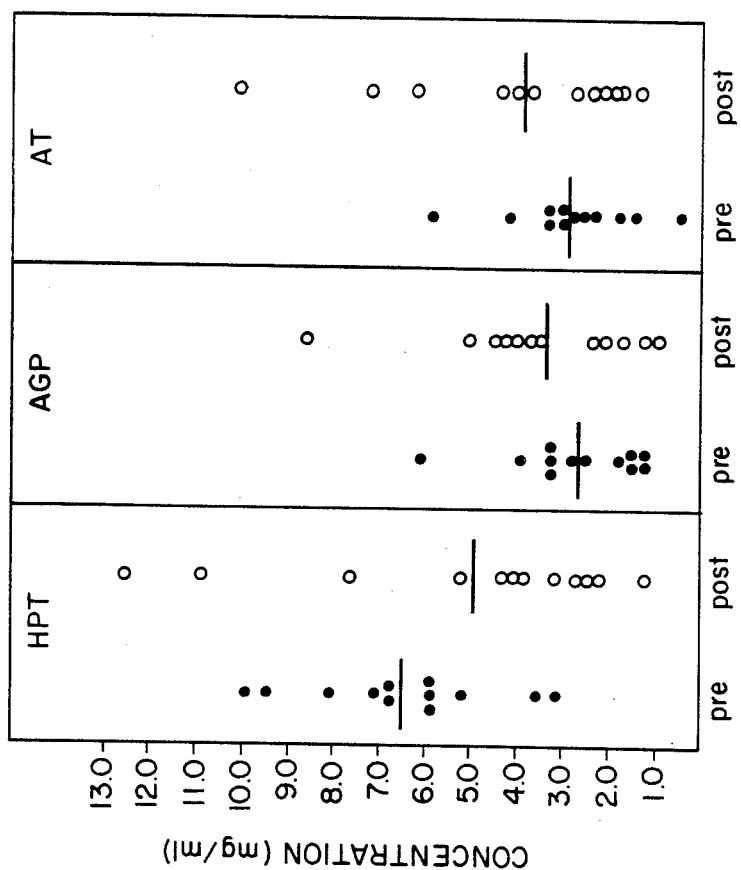

FIG. 4 represents the changes in the levels of the APP in the twelve patients who did not respond to therapy. Nonresponders encompass three patients who have expired and nine patients still demonstrating progressive disease while on therapy. Eight of the nine progressors had elevated pretreatment levels of Hpt. Although Hpt levels decreased in eight of nine patients over the course of therapy, levels remained higher than normal in four of these patients and one patient even experienced rising levels. All nine progressors had pretreatment levels of AGP above the normal range. Four of these nine demonstrated increases at least three months beyond initial treatment. The remaining five patients demonstrated slight decreases or no change. At final evaluation, all patients with progressive tumor still had levels of AGP greater than normal. Six of the nine progressors began with levels of AT greater than normal. Seven of these nine demonstrated increases over the course of therapy and all patients except one still had levels remaining above normal at final evaluation. These nine progressors had levels of CRP which ranged from 6.2 to 72.0 (ug/ml) and levels of albumin which ranged from 26.8 to 53.1 (mg/ml) over the course of therapy. These nine progressors experienced a significant mean decrease in Hpt from $6.1\pm0.7$ to $4.25\pm0.9$, $p<0.01$, but the level of reduction was less than that seen in the responders. Increases in AGP from $2.64\pm5$ to $3.28\pm0.8$ and in AT from $2.33\pm0.3$ to $3.12\pm0.5$ were not significant as analyzed by the Student's t test ($p<0.1$ for AGP and $p<0.2$ for AT).

Changes Observed in APP in Expired Patients

All three expired patients demonstrated pretreatment levels of Hpt in the acute phase range at or prior to the first treatment and two of these patients had levels remaining at least two fold greater than normal levels at the time of expiration. All three patients began with AGP levels in the acute phase range and all demonstrated increases over time. Similarly, all three had initial AT levels above normal and two demonstrated increases over time to levels 3 to 5 time greater than the normal value at the time of death. These results have been summarized in FIG. 4. Levels of CRP ranged from 32.0 to 100.0 (ug/ml) indicating possible secondary infection and levels of albumin ranged from 21.8 tp 43.8 (mg/ml) suggesting that some of these patients might have cachexia. These 3 patients experienced a significant increase in Hpt from $5.04\pm1.6$ to $6.8\pm2.4$, $p<0.05$, but increases in AGP from $2.33\pm0.2$ to $3.7\pm0.1$ and in AT from $4.38\pm0.6$ to $6.34\pm2.0$ which were not significant as analyzed by the Student's t test ($p<0.1$ for AGP amd $p<0.2$ for AT).

Changes Observed in Serum Levels of SER in all Patients

Eight of the nine patients who responded to autolymphocyte therapy had initial SER levels below the normal value (1.06). It is interesting to note that the one patient who had a high level of SER prior to treatment demonstrated a dramatic decrease to a level below normal within the first month of therapy (Table IV). Of the seven patients responding to therapy and followed sequentially for SER levels, six demonstrated decreases and one demonstrated a slight increase but to a level still remaining at least 50% below normal. Within the nine progressing patients, five had levels of SER above the normal value and three of the four with normal initial levels had increases over the course of therapy. Interestingly, it is known that at least one of these four progressors underwent radiation therapy prior to immunotherapy which could explain the low SER levels observed in this patient prior to treatment. Three of four patients who expired had extraordinarily high levels of SER prior to treatment. Although levels of SER decreased over the course of therapy, they remained at levels above normal at the time of death.

Comparison of SER with Other Immune Interfering Substances

In order to determine whether the level of SER in patient serum can serve as a better indicator of immune suppression than other immune interfering substances, levels of SER were compared to levels of immunosuppressive acidic protein (IAP), circulating immune complexes (CIC) and CA 125 antigen in the sera of patients undergoing autolymphocyte therapy. Of the 22 patients examined (Table V), seven belonged to group A and reached stable condition, five belonged to group B and expired before six months, four belonged to group C and D and expired before six months, and two belonged to group E with progressing tumors.

IAP is analagous to AGP but has a reduced sialic acid content and has been proven to be a more efficient indicator of tumor burden than carcinoembryonic antigen in monitoring gynecological malignancies. As seen in Table V, elevated levels of IAP in these renal cell carcinoma patients provides a poor patient prognosis. Levels of IAP in each patient were rather insensitive to the progression of tumor or the course of therapy. On the other hand, the levels of CIC were high in patients who either reached a stable condition or expired and were low in those patients with progressive tumors. Therefore, CIC levels appear to have very little correlation with patient's tumor burden.

CA 125 antigen is an ovarian tumor antigen, but is also found in many other types of tumors as well as benign diseases (Centocor clinical data, Centocor Inc.-,Malvern, Pa.). Since SER was originally isolated from the ascites fluid of ovarian tumor bearing patients and no other tumor markers are available in patients with renal cell carcinoma, levels of CA 125 were examined in comparison to levels of SER. As shown in Table V, 12 of 22 (50%) of the patients listed in groups (A) and (B) had levels of SER and CA 125 antigen which were both either high or low. However, the elevated levels of SER seen in group (C) and levels of CA 125 antigen in group (D) showed discrepancies within their distribution in the patient population. All three antigens, i.e., SER, IAP and CA 125 failed to detect the course of therapy in patients in group (E), while the normal acute phase reactants Hpt and AGP and CIC showed marked elevation. It is not known whether the patients in this group had tumors of high antigenic strength thus producing antigen-antibody complexes and/or or were on other therapy such as steroid therapy which could induce high levels of the APP.

This example demonstrares several interesting relationships among the various immunoregulatory proteins examined. The most significant findings were revealed upon analysis of levels of Hpt, AGP, AT and SER in sequential serum samples drawn from renal cell carcinoma patients treated with autolymphocyte therapy. In order to compare relative changes of one APP over another for clinical monitoring purposes, mean values were obtained for pretreatment and posttreatment levels of Hpt, AGP and AT in patients responding, progressing or expiring following autolymphocyte therapy. These results are illustrated in FIGS. 3 and 4.

The most significant mean change in pretreatment and posttreatment Hpt levels was observed in patients responding to therapy (i.e., $6.08\pm0.8$ to $1.62\pm0.2$) while a significant decrease from $6.1\pm0.7$ to $4.25\pm0.9$ was observed for those progressing upon treatment. Those patients who expired actually demonstrated a mean increase from $5.05+1.6$ to $6.8+2.4$. Despite the fact that both responders and progressors demonstrated decreased Hpt levels following treatment, only the responders consistently showed levels failing below normal value. Thus, a decrease in haptoglobin to a level below normal is suggestive that a patient is or has the potential to respond to autolymphocyte therapy while increasing levels suggest a patient may not be responding favorably to this type of treatment. Conversely, abnormally high levels of Hpt does not necessarily mean they do not have the potential to respond to treatment. Therefore, Hpt is a sensitive indicator of patients' immune status but may not serve as an optimal prognostic marker.

The general trends observed for alterations in AGP levels suggests that those patients responding to therapy are more likely to demonstrate decreasing levels of AGP while non-responding patients demonstrate increasing or unchanging levels. In fact, 8 of 9 (89%) responders demonstrated decreases in AGP levels compared to only 4 of 12 (33%) nonresponders demonstrating similar decreases. Upon examination of the mean pretreatment and posttreatment AGP levels, it can be seen that only those patients responding to treatment demonstrated a mean decrease while patients progressing or expiring demonstrated mean increases. In fact, those patients responding experienced a significant decrease from $3.08\pm0.6$ to $1.37\pm0.2$, while those progressing or expiring experienced an increase from $2.64\pm0.5$ to $3.28\pm0.7$ and from $2.33\pm0.2$ to $3.7\pm0.1$ respectively. In this study, AGP levels did correlate with patients' status and appears to be a useful protein to monitor as an indication of failure to treatment. In contrast to AGP, however, decreases in Hpt levels appear to be a more sensitive indicator for patients responding to therapy.

AT levels tended to increase in all patients examined regardless of their response to autolymphocyte therapy although the elevations observed in the nonresponders were generally more dramatic. Thus, levels of AT, at least in this renal cell carcinoma, melanoma, and pancreatic cancer panel, did not appear to reflect the course of response to therapy. It is not known what causes the elevation in AT in these patients nor is it known whether these increases are specific to this adoptive immunotherapy or any other anti-cancer treatments.

Although no general trends were observed for alterations in CRP levels in these patients undergoing autolymphocyte therapy, levels of CRP are included as an indicator of disease activity, particularly if the tumor load is large enough to produce tissue damage, and to monitor secondary infection in such immunosuppressed patients. It should be noted that three patients with active bacterial (*Klebsiella pneumoniae*, Staphlycoccal) or yeast infections, listed in Table III, had levels of CRP significantly higher than levels observed in any of the 21 patients undergoing autolymphocyte therapy. Thus, CRP levels ten fold or greater than normal may be related more to infection than tumor load. Although general trends for alterations in albumin levels were not observed, only those patients not responding to therapy demonstrated acute phase levels of albumin. Since albumin decreases during the APR and in malignancy while the other APP observed increase, levels of albumin should be monitored as a negative control and as an indicator of cachexia. Despite the limitation that the APP respond specifically to tissue injury and infection, detection of these changes can be determined prior to changes detected by physical examination or radiographic studies and may prove useful information on the patients' clinical status to the physician.

Obviously, if one is to accurately evaluate immune status, focus should be placed on the immunosuppressive factors associated with malignant disease and found in very low quantities if at all in normal individuals. haptoglobin. Furthermore, as indicated in Table V, levels of SER are a more definitive prognostic marker than levels of IAP, CIC or CA 125. SER levels greater than ten times normal levels were observed in patients who were progressing or who expired compared to IAP levels in the same serum sample which were only 2 fold greater than normal.

TABLE I

Acute Phase Proteins and SER levels in sera of Normal Adults.

|  | HPT (mg/ml) | AGP (mg/ml) | AT (mg/ml) | CRP (μg/ml) | SER (μg/ml) |
|---|---|---|---|---|---|
| Average normal values (mean ± SE)[a] | 2.88 ± .18 | 0.68 ± .07 | 1.75 ± .13 | 5.11 ± 2.5 | 1.06 ± .05 |
| Reported normal values[b] | 1.0–2.0 | 0.6–1.2 | 1.5–3.0 | 1.0 | NA[c] |
| Reported acute phase levels[b] | 5.0–6.0 | 1.5–2.5 | 4.0–6.0 | 300–500 | NA |

[a]Mean ± standard error. Values represent an average of quadrupliate determinations except for haptoglobin which was determined twice in quadruplicate in 19 normal adults.
[b]See reference 2
[c]NA = not available.
Hpt, haptoglobin; AGP, alpha-1-acid glycoprotein; AT, alpha-1-antitrypsin; CRP, C-reactive protein; SER, suppressive E-receptor factor.

Thus, SER, which specifically inhibits T cell function in vitro and in vivo, has been examined in pateints with malignant disorders. The findings in this example show use of SER as one of the most useful components to be observed as an indication of a patient's immune status and subsequent response to therapy. In the patients undegoing immunotherapy in this example, highly elevated levels of SER correlated with a lack of response to therapy and most significantly with a poor prognosis for survival. Low pretreatment levels of SER or decreases to levels below normal are associated with those individuals who are likely to respond to an adoptive immunotherapy regimen whereas levels elevated above normal or increases over the pretreatment levels are associated with a disease progression depite the therapy. Furthermore, the values for SER in the patients examined in this example show the smallest range of deviation in the normal population when compared to the deviations determined for the APP measured.

Although SER represents a variant of haptoglobin, the levels of SER and adult haptoglobin measured in this study do not correlate each other and SER levels are the better predictor of patient response. Furthermore, SER has been shown to be 1000 times more suppressive than normal human Hpt (46). Such analysis implicates SER levels as a more reliable diagnostic and prognostic marker of immune status than normal adult

TABLE II

Acute Phase Proteins in the Plasma or Serum of Patients with Autoimmune Diseases and Cancer.

| Diagnosis | HPT | AGP | AT |
|---|---|---|---|
| Guillain-Barre A. | 0.70[a] | 2.04 | 1.15 |
| Guillain-Barre B. | 1.60 | 1.02 | 1.80 |
| Peripheral neuropathy | 2.50 | 2.20 | 2.48 |
| Myasthenia Gravis A. | 2.50 | 2.20 | 2.40 |
| Myasthenia Gravis B. | 0.96 | 2.16 | 1.30 |
| Dermatitis (↑IgE) | 3.78 | 1.68 | 0.38 |
| Thrombocytosis | 3.60 | 4.40 | 7.20 |
| IgM myeloma A. | 2.10 | 3.00 | 4.70 |
| IgM myeloma B. | 3.38 | 0.80 | 1.50 |
| IgG myeloma | 5.80 | 4.44 | 3.90 |
| Multiple myeloma | 4.50 | 2.30 | 1.35 |
| Head and Neck Cancer: | | | |
| Stable condition | 1.65 | 1.44 | 0.74 |
| Progressive tumor | >10.00 | 5.58 | 3.30 |
| Expired | 2.80 | 7.40 | 6.40 |
| Renal Cell Carcinoma: | | | |
| Complete response | 1.90 | 1.20 | 2.40 |
| Stable condition | 1.05 | 1.90 | 3.00 |
| Progressive tumor | 3.90 | 8.60 | 6.20 |
| Expired | 12.50 | 4.00 | >10.00 |
| Normal Values (mean ± S.E.) | 2.88 ± .18 | 0.68 ± .07 | 1.75 ± .13 |

[a]Values represent an average of quadruplicate determinations on individual patients unless otherwise indicated.
HPT, haptaglobin; AGP, alpha-1-acid glycoprotein; AT, alpha-1-antitrypsin. Concentrations in mg/ml.

TABLE III

Acute Phase Proteins in Plasma or Sera of Patients with Bacterial, Viral and Yeast Infections.

| Diagnosis | # of Patients[a] | HPT (mg/ml) | AGP (mg/ml) | Albumin (mg/ml) | CRP (μg/ml) |
|---|---|---|---|---|---|
| *Klebsiella pneumoniae* | 3 | 8.9 | 0.6 | 42.4 | 205.0 |
| *Pseudomonas aeruginosa* | 1 | 1.6 | 1.6 | 28.8 | 46.5 |
| *Haemophilus influenzae* | 1 | 1.5 | 2.7 | 30.1 | 35.0 |
| *Corynebacterium diptheriae* | 1 | 3.1 | 1.6 | ND[b] | 49.0 |
| Streptococcus | 2 | 2.4 | 0.6 | 35.6 | 55.0 |
| Staphylococcus | 3 | 6.6 | 1.1 | 21.6 | 180.0 |
| Campylobacter | 1 | 0.6 | 0.3 | 25.6 | 25.0 |
| *Escherichia coli* | 2 | 6.4 | 0.7 | 43.2 | 90.0 |
| Yeast | 1 | 1.7 | 1.1 | 25.6 | 132.0 |
| Epstein Barr Virus | 4 | 0.9 | 2.3 | 29.3 | 34.0 |

TABLE III-continued

Acute Phase Proteins in Plasma or Sera of
Patients with Bacterial, Viral and Yeast Infections.

| Diagnosis | # of Patients[a] | HPT (mg/ml) | AGP (mg/ml) | Albumin (mg/ml) | CRP (μg/ml) |
|---|---|---|---|---|---|
| Normal values: (mean ± SF) | | 2.88 ± .18 | 0.68 ± .07 | 34.5 ± .74 | 5.11 ± 2.5 |

[a]Indicates the number of patients examined with the particular infection. The average protein values for one of these patients is provided. Standard deviation was below 10% in all samples.
[b]ND = Not Determined.
HPT, Haptoglobin; AGP, alpha-1-acid glycoprotein; CRP, C-reactive protein.

TABLE IV

Changes in the Levels of SER in Patients Undergoing Autolymphocyte Therapy.

| Patients | Pretreatment Levels Above Normal[a] | Posttreatment Levels Above Normal | Increase in SER Levels[b] | Decrease in SER Levels[c] | No Change in SER Levels |
|---|---|---|---|---|---|
| RESPONDERS (7)[d] | 1/7 | 0/7 | 1/7 | 6/7 | 0/7 |
| PROGRESSORS (9) | 5/9 | 3/9 | 3/9 | 5/9 | 1/9 |
| EXPIRED (4) | 3/4 | 3/4 | 0/4 | 4/4 | 0/4 |

[a]SER normal level is 1.06 ± 0.05 μg/ml.
[b]An increase in SER levels at least 10% above pretreatment levels three months or beyond initiation of treatment.
[c]A decrease in SER levels at least 10% below pretreatment levels three months or beyond initiation of treatment.
[d]Responders encompass individuals with a complete or partial response to therapy or in stable condition.

TABLE V

Comparison of SER with other Immune Parameters

| Date taken | IAP[a] (mg/ml) | AGP[b] (mg/ml) | HPT[c] (mg/ml) | SER[d] (μg/ml) | CIC[e] (μg/ml) | CA125[f] (unit/ml) |
|---|---|---|---|---|---|---|
| (A) | | | | | | |
| 4/16/86 | 0.743 | 3.05 | 3.90 | 0.74 | 11.0 | 18 |
| 5/16/86 | 0.657 | 1.90 | 2.40 | 1.25 | 11.2 | 18 |
| 6/17/86 | 0.550 | 1.40 | 2.90 | 0.30 | 5.3 | 15 |
| 7/21/86 | 0.700 | 1.20 | 3.20 | 0.20 | 8.4 | 18 |
| 8/18/86 | ND[g] | 1.50 | 3.20 | 0.30 | 14.2 | 16 |
| (B) | | | | | | |
| 3/19/86 | 1.203 | 3.10 | 7.00 | 4.20 | 6.9 | 30 |
| 4/18/86 | 1.300 | 4.20 | 9.70 | 4.60 | 5.3 | 32 |
| 5/19/86 | 1.86 | 3.15 | 6.95 | >10.00 | 4.2 | 50 |
| 6/20/86 | ND | 3.60 | 5.20 | 2.00 | 14.0 | 65 |
| 7/22/86 | ND | 4.30 | 3.20 | 1.80 | 12.0 | 120 |
| (C) | | | | | | |
| 6/11/86 | 0.980 | 3.80 | 16.00 | 3.20 | 3.6 | 20 |
| 7/28/86 | 1.061 | 1.70 | 6.80 | 1.35 | 2.4 | 20 |
| 8/25/86 | 1.042 | 1.45 | 9.30 | 4.30 | 2.5 | 20 |
| 9/26/86 | 1.020 | >10.00 | 3.70 | 1.60 | 2.0 | 30 |
| (D) | | | | | | |
| 6/10/86 | 1.193 | 6.00 | 5.80 | 0.10 | <2.0 | 25 |
| 7/13/86 | 1.386 | ND[g] | 4.10 | 0.80 | <2.0 | ND |
| 8/11/86 | 1.321 | ND | 5.15 | 0.38 | <2.0 | ND |
| 9/12/86 | 1.676 | 9.20 | 2.60 | 0.58 | <2.0 | 105 |
| 10/14/86 | 1.471 | 4.90 | 3.80 | 0.46 | 2.7 | 215 |
| (E) | | | | | | |
| 3/21/86 | 1.178 | 3.09 | 7.00 | 1.40 | 19.4 | <6.5 |
| 4/25/86 | 0.907 | 2.10 | 5.80 | 1.00 | 23.6 | <6.5 |
| 5/27/86 | 1.000 | 1.80 | 5.20 | 0.50 | 12.2 | <6.5 |
| 6/24/86 | 1.000 | 2.60 | 5.60 | 0.22 | 12.0 | <6.5 |
| 7/28/86 | 0.939 | 2.00 | 8.20 | 0.23 | 5.8 | <6.5 |
| 8/25/86 | 0.876 | 2.00 | 6.60 | 0.33 | 7.0 | <6.5 |

[a]IAP, immunosuppressive acidic protein. Normal = 600 mg/L.
[b]AGP, alpha-1-acid glycoprotein. Normal = 0.68 ± .07 mg/ml.
[c]HPT, haptoglobin. Normal = 2.88 ± .18 mg/ml.
[d]SER, suppressive E-receptor factor. Normal = 1.06 ± .05 μg/ml.
[e]CIC, circulating immune complex. Normal = 10 μg/ml.
[f]CA 125, Cancer Antigen 125. Normal = females 10.7 ± 9.6 units/ml; males 8.0 ± 8 units/ml.
[g]ND = not determined.

Figure-Caption List

FIG. 1. Standard curves for Hpt, AGP, AT and CRP as assessed by ELISA. Each point represents a mean value of quadruplicate determinations.

FIG. 2. Concentration of Hpt versus SER using the murine monoclonal antibody AH7B8 as the primary antibody for ELISA analysis. AH7B8 detects only background levels of Hpt and shows dose-responsiveness to varying concentrations of SER. AH7B8 was used to determine SER levels in patients' sera.

FIG. 3. Comparison of mean pretreatment and posttreatment values of Hpt, AGP and AT in nine patients responding to autolymphocyte therapy. Each point represents an average pretreatment (•) or posttreatment (o), protein level for an individual patient. Posttreatment levels were determined at least three months following the initiation of treatment. The bar represents the average value for that set of data. Hpt and AGP levels decreased significantly from $6.08 \pm 0.8$ (means$\pm$SE) to $1.62 \pm 0.2$ ($p < 0.001$) and from $3.08 \pm 0.6$ to $1.37 \pm 0.2$ ($p < 0.05$) respectively. AT increased significantly from $2.56 \pm 0.2$ to $3.38 \pm 0.3$ ($p < 0.01$). Levels of significance were determined by the Student's t test.

FIG. 4. Comparison of mean pretreatment and posttreatment levels of Hpt, AGP and AT in twelve patients not responding to autolymphocyte therapy. Each point represents an average pretreatment (•) or posttreatment (o) protein level for an individual patient. Posttreatment levels were determined at least three months following the initiation of treatment. The bar represents the average value for that set of data. Hpt levels decreased significantly from $6.43 \pm 0.6$ (mean$\pm$SE) to $4.89 \pm 0.9$ ($p < 0.001$). AGP and AT increased significantly from $2.56 \pm 0.4$ to $3.39 \pm 0.6$ ($p < 0.05$) and from $2.85 \pm 0.4$ to $3.93 \pm 0.7$ ($p < 0.01$) respectively. Levels of significance were determined by the Student's t test.

I claim:

1. A process for detecting cancer in a human patient, wherein the body of said patient produces an immunosuppressive factor, which comprises contacting a body fluid of the patient with an antibody that reacts with a haptoglobin variant of said immunosuppressive factor under conditions to effect an immunoreaction between said antibody and said haptoglobin variant when said immunosuppressive factor is present in said body fluid, said varient of haptoglobin comprising a beta subunit of a molecular weight of 38-40K Daltons covalently bonded to a second alpha-subunit of a molecular weight of 17-19K Daltons, detecting said immunoreaction wherein an increase of immunosuppressive factor in said patient is an indication of cancer.

2. The process for monitoring the effect of a cancer therapy to a human patient, wherein the body of said patient produces an immunosuppressive factor, which comprises contacting at regularly spaced intervals a body fluid of the patient after said cancer therapy with an antibody that reacts with a haptoglobin variant of said immunosuppressive factor under conditions to effect an immunoreaction between said antibody and said haptoglobin variant when said immunosuppressive factor is present in said body fluid, said varient of haptoglobin comprising a beta subunit of a molecular weight of 38-40K Daltons covalently bonded to a second alpha-subunit of a molecular weight of 17-19K Daltons, wherein an increase of immunosuppressive factor in said patient is an indication of cancer, determining the concentration of said factor from said reaction and comparing said concentration to a second concentration obtained by said process with a second sample of said fluid.

* * * * *